United States Patent
Marom et al.

(10) Patent No.: US 9,102,592 B2
(45) Date of Patent: Aug. 11, 2015

(54) INTERMEDIATE COMPOUNDS AND PROCESSES FOR THE PREPARATION OF QUINOLINE DERIVATIVES SUCH AS LAQUINIMOD SODIUM

(71) Applicant: MAPI PHARMA LTD., Ness Ziona (IL)

(72) Inventors: Ehud Marom, Kfar Saba (IL); Michael Mizhiritskii, Rehovot (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 14/471,951

(22) Filed: Aug. 28, 2014

(65) Prior Publication Data

US 2015/0051419 A1    Feb. 19, 2015

Related U.S. Application Data

(62) Division of application No. 13/989,910, filed as application No. PCT/IL2011/050030 on Nov. 28, 2011, now Pat. No. 8,865,742.

(60) Provisional application No. 61/417,431, filed on Nov. 28, 2010.

(51) Int. Cl.
| | |
|---|---|
| *C07D 215/00* | (2006.01) |
| *C07D 215/22* | (2006.01) |
| *C07C 233/55* | (2006.01) |
| *C07C 63/70* | (2006.01) |
| *C07C 233/11* | (2006.01) |
| *C07D 221/02* | (2006.01) |
| *C07C 235/78* | (2006.01) |
| *C07C 229/56* | (2006.01) |

(52) U.S. Cl.
CPC .............. *C07C 235/78* (2013.01); *C07C 63/70* (2013.01); *C07C 229/56* (2013.01); *C07C 233/11* (2013.01); *C07C 233/55* (2013.01); *C07D 215/00* (2013.01); *C07D 215/22* (2013.01)

(58) Field of Classification Search
USPC ........................................ 564/442, 168, 200
See application file for complete search history.

(56) References Cited

U.S. PATENT DOCUMENTS

| | | | |
|---|---|---|---|
| 4,633,009 A | 12/1986 | Lerner | |
| 6,077,851 A | 6/2000 | Bjork et al. | |
| 6,844,435 B2 * | 1/2005 | Snow et al. | 544/250 |
| 6,875,869 B2 | 4/2005 | Jansson | |
| 7,560,557 B2 | 7/2009 | Jansson | |
| 8,865,742 B2 * | 10/2014 | Marom et al. | 514/321 |
| 2007/0088050 A1 | 4/2007 | Frenkel et al. | |
| 2010/0055072 A1 | 3/2010 | Gant et al. | |

FOREIGN PATENT DOCUMENTS

| | | | |
|---|---|---|---|
| GB | 2236318 A | | 4/1991 |
| JP | 07224040 | | 8/1995 |
| WO | WO 9218483 | * | 10/1992 |
| WO | 02/28818 A1 | | 4/2002 |
| WO | 2006/072370 A1 | | 7/2006 |
| WO | 2007/047863 A2 | | 4/2007 |
| WO | 2009/133468 A1 | | 11/2009 |
| WO | 2010/001257 A2 | | 1/2010 |
| WO | 2010/028015 A2 | | 3/2010 |
| WO | 2012/070051 A1 | | 5/2012 |

OTHER PUBLICATIONS

Hsieh; Bioorganic and Medicinal Chemistry Letters, 2007, 17, 1812-1817.*
Kerns; Drug-like Properties Concepts, Structure Design and Methods from ADME to Toxicity Optimization, Elsevier, 2008, chapter 8, pp. 86-99.*
West; Journal of the Chemical Society, Transactions, 1925, 127, 748-753.*
Beutner et al., (2007) A practical method for preparation of 4-hydroxyquinolinone esters. J Org Chem 72(18): 7058-61.
Roma et al., (1987) 1,2-Fused pyrimidines. III. Derivatives of 12H—pyrido[1',2':1,2]pyrimido[4,5—b]quinoline, a novel heterocyclic system. Journal of Heterocyclic Chemistry 24(2):329-335.
Tsuji et al., (2002) Synthesis and antinephritic activities of quinoline-3-carboxamides and related compounds. Bioorg Med Chem Lett 12(1): 85-8.
Supplementary European search report of EP patent application No. 11842945.5, dated Apr. 28, 2014.
Ukrainets; Chemistry of Heterocyclic Compounds, 1993, 29, 1041-1043.
González et al., (2009) Selective monomethylation of anilines by Cu(OAc)2-promoted cross-coupling with MeB(OH)2. Org Lett 11(8): 1677-1680.
Jansson et al., (2006) Synthesis and reactivity of laquinimod, a quinoline-3-carboxamide: intramolecular transfer of the enol proton to a nitrogen atom as a plausible mechanism for ketene formation. J Org Chem 71(4): 1658-1667.
Katagi et al., (1985) Syntheses and antiinflammatory activity of malonamic acid, malonamate and malonamide derivatives of some heterocyclic compounds. Chem Pharm Bull 33(11): 4878-4888.
Rigo et al., (1989) Reaction of trimethylsilyl derivatives with Meldrum's acid : A new and easy monofunctionalization of malonic acid. Tetrahedron Lett 30(23): 3073-3076.

(Continued)

*Primary Examiner* — John Mabry
*Assistant Examiner* — Daniel Carcanague
(74) *Attorney, Agent, or Firm* — Rothwell, Figg, Ernst & Manbeck, P.C.

(57) ABSTRACT

The present invention relates to processes for the preparation of quinoline-3-carboxamide derivatives, such as sodium 5-chloro-3-(ethylphenylcarbamoyl)-1-methyl-2-oxo-1,2-dihydroquinolin-4-olate (Laquinimod sodium). The present invention further relates to intermediates formed in such processes.

4 Claims, No Drawings

(56) References Cited

OTHER PUBLICATIONS

Savinov and Austin (2002) Modular evolution of a chiral auxiliary for the 1,3-dipolar cycloaddition of isomünchnones with vinyl ethers. Org Lett 4(9): 1415-1418.

Wennerberg et al., (2007) Development of a Practical and Reliable Synthesis of Laquinimod. Organic Process Research & Development 11(4): 674-680.

Pronk et al. Anthanilate Derivatives, 2006, retrieved on Apr. 7, 2012; especially p. 2 http://libdoc.who.int/publications/2006/9241660562_part2_d_eng.pdf.

3-[(4-Methoxyphenyl)Amino]-3-Oxopropanoic Acid, 2008, p. 1. Retrieved from http://www.chemicalbook.com/ProdSupplierGWCB92455731_EN.htm on Apr. 7, 2012.

* cited by examiner

INTERMEDIATE COMPOUNDS AND PROCESSES FOR THE PREPARATION OF QUINOLINE DERIVATIVES SUCH AS LAQUINIMOD SODIUM

CROSS REFERENCE TO RELATED APPLICATIONS

The present application is a divisional of U.S. patent application Ser. No. 13/989,910, filed on May 28, 2013, which is a 35 U.S.C. §371 National Phase Entry Application from PCT/IL2011/050030, filed Nov. 28, 2011, and designating the United States, which claims the benefit of U.S. Patent Application No. 61/417,431 filed Nov. 28, 2010, which are incorporated herein in their entireties.

FIELD OF THE INVENTION

The present invention relates to processes for the preparation of quinoline-3-carboxamide derivatives, such as sodium 5-chloro-3-(ethylphenylcarbamoyl)-1-methyl-2-oxo-1,2-dihydroquinolin-4-olate (Laquinimod sodium). The present invention further relates to intermediates formed in such processes.

BACKGROUND OF THE INVENTION

Laquinimod sodium, also known as a sodium 5-chloro-3-(ethylphenylcarbamoyl)-1-methyl-2-oxo-1,2-dihydroquinolin-4-olate, ALLEGRO, ABR-215062 sodium or TV-5600 is a once-daily, orally administered immunomodulatory compound that was developed as a disease-modifying treatment for relapsing remitting multiple sclerosis (RRMS). Laquinimod has demonstrated potent therapeutic efficacy in preclinical and clinical models of other autoimmune diseases such as Crohn's disease, rheumatoid arthritis, insulin-dependent diabetes mellitus, Guillain Barré Syndrome, and Lupus.

Several patents, patent applications (U.S. Pat. No. 6,077,851, U.S. Pat. No. 6,875,869, U.S. Pat. No. 7,560,557, WO 2009/133468 and WO 2010/028015) and scientific publications (Jansson et al., J. Org. Chem. 2006, 71, 1658-1667; and Wennerberg et al., Organic Process Research & Development, 2007, 11, 674-680) disclose the compound Laquinimod, its pharmacological activity and processes for its preparation. The typical preparation scheme is summarized below (Scheme 1):

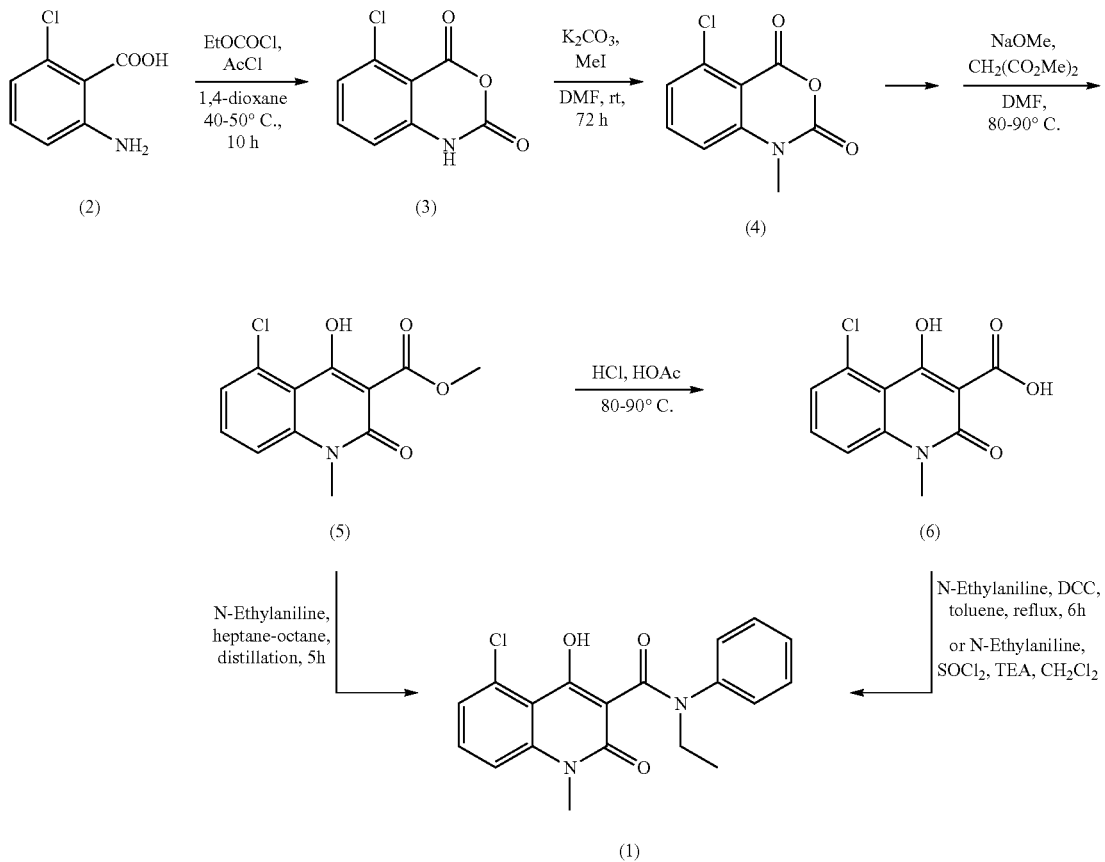

The aforementioned methods for Laquinimod synthesis are based on the intermediate 1,2-dihydro-4-hydroxy-5-chloro-1-methyl-2-oxo-quinoline-3-carboxylic acid (6) and its alkyl(methyl)ester (5). The main disadvantage of such approaches is facile decarboxylation of acid (6) under basic and acidic conditions (see, Wennerberg et al.), that leads to a significant decrease in the yield of the final product and complicates the stage of final product purification and sodium salt formation. Even methyl ester (5) demands completely anhydrous conditions for handling. With this background, a synthetic sequence more suitable for large scale preparation of Laquinimod and other quinolin-3-carboxamide derivatives is desirable.

SUMMARY OF THE INVENTION

The present invention provides processes for preparing quinolin-3-carboxamide derivatives such as Laquinimod and its pharmaceutically acceptable salts. The present invention further relates to certain intermediates in such processes.

As contemplated herein, the present invention generally relates to a process for the preparation of quinolin-3-carboxamide derivatives of general formula (I)

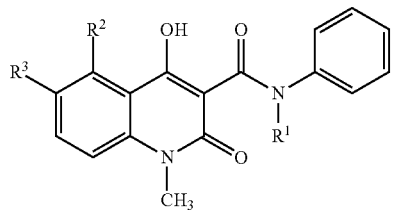
(I)

or a salt thereof, wherein $R^1$ is selected from hydrogen, methyl, ethyl, n-propyl, iso-propyl, n-butyl, iso-butyl, sec-butyl and allyl;

$R^2$ is selected from methyl, ethyl, n-propyl, iso-propyl, methoxy, ethoxy, halogen, trifluoromethyl and trifluoromethoxy;

$R^3$ is hydrogen; or $R^2$ and $R^3$ together are selected from methylenedioxy, ethylenedioxy and isopropylidenedioxy.

The process comprises the steps of:

a) reacting an anthranilate derivative of formula (7A)

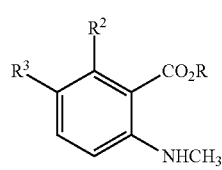
(7A)

wherein R is an alkyl, aryl or alkylaryl, with a 3-oxopropanoic acid derivative of formula (8A)

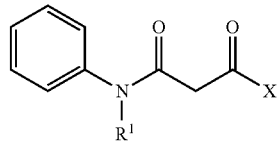
(8A)

wherein X is OH or a leaving group, so as to obtain a compound of formula (9A):

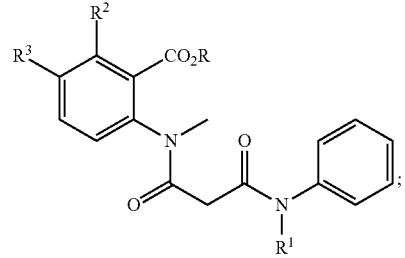
(9A)

and b) converting (i.e., cyclizing) compound (9A) obtained in step (a) to a compound of formula (I), or a salt thereof, in the presence of a base.

Preferably the salt is a pharmaceutically acceptable salt.

Alternatively, in another embodiment, compound (9A) can first be converted to an activated ester derivative thereof by saponifying the ester group $CO_2R$ in compound (9A) to the corresponding carboxylic acid $CO_2H$ so as to obtain a compound formula (10A), and converting acid (10A) to an activated derivative thereof of formula (11A):

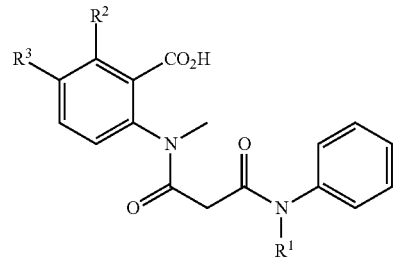
(10A)

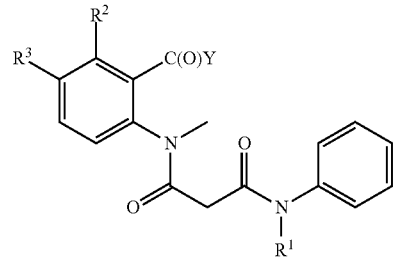
(11A)

wherein Y is a leaving group. Compound (11A) is then converted (cyclized) to the compound of formula (I), or a salt thereof, in the presence of a base and optionally further in the presence of a Lewis acid.

In one currently preferred but non-limiting embodiment, the process described in the present application is used to prepare a compound of formula (I) wherein $R^1$ is ethyl, $R^2$ is chloro and $R^3$ is H. This compound is Laquinimod, which is represented by the structure of formula (1), or a salt thereof, such as the sodium salt:

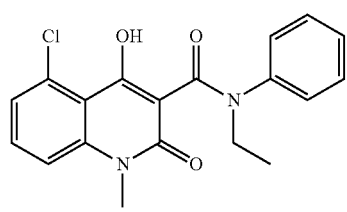
(1)

In accordance with this embodiment, the process comprises the steps of:

a) reacting N-methyl 6-chloroanthranilate of formula (7)

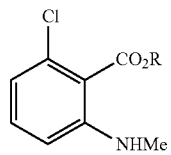
(7)

wherein R is an alkyl, aryl or alkylaryl, with 3-(ethyl(phenyl)amino)-3-oxopropanoic acid derivative of formula (8)

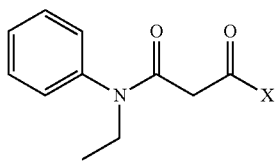
(8)

wherein X is OH or a leaving group, so as to obtain 2-chloro-6-(3-(ethyl(phenyl)amino)-N-methyl-3-oxopropanamido)benzoate of formula (9)

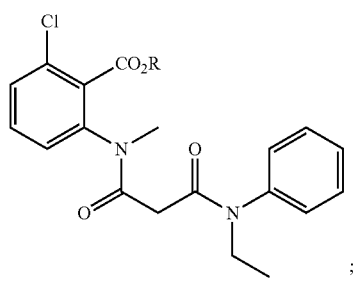
(9)

and b) converting (i.e., cyclizing) compound (9) obtained in step (a) to Laquinimod (1), or a salt thereof, in the presence of a base.

Alternatively, in another embodiment, compound (9) obtained in step (a) can first be converted to an activated ester derivative thereof by saponifying the ester group $CO_2R$ in compound (9) to the corresponding carboxylic acid $CO_2H$ so as to obtain a compound formula (10), and converting acid (10) to an activated derivative thereof of formula (11):

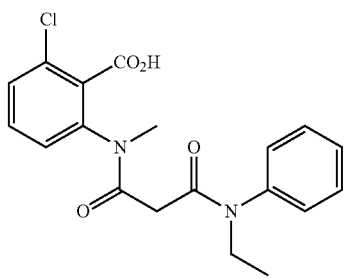
(10)

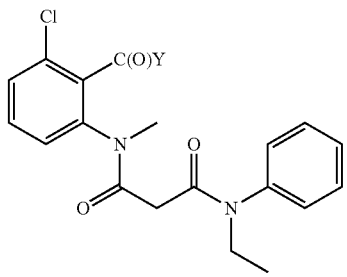
(11)

wherein Y is a leaving group. Compound (11) is then converted (cyclized) to Laquinimod of formula (1), or a salt thereof in the presence of a base and optionally further in the presence of a Lewis acid.

In one embodiment, the step of converting compound (11A) to compound (I) in the presence of a base directly produces the salt of compound (I). In another embodiment, the step of converting compound (11) to compound (1) in the presence of a base directly produces the salt of compound (1) (Laquinimod). An acid can then optionally be added to convert the salt of compound (I) or (1) to the corresponding acidic form (i.e., enol) and, if desired, a base can be added to form the salt form of compound (I) or (1). Each possibility represents a separate embodiment of the present invention.

The R group in the intermediate compounds used in the processes described herein is an alkyl, aryl, or arylalkyl. Preferably, R is methyl, ethyl or benzyl.

The X and Y groups used in the processes described herein are each a leaving group, for example a halogen (F, Cl, Br or I), or a sulfonyloxy (e.g., mesylate (OMs), triflate (OTr), tosylate (OTs) and the like). Other examples of X and Y include, but are not limited to OBt, ONSu or OC(O)R' wherein R' is an alkyl, aryl or arylalkyl. Other suitable leaving groups are further described hereinbelow. Preferably, each of X and Y is a halogen, for example Cl. In another preferred embodiment, X is OH.

Step (a) of the process, i.e., reaction of compound (7A) with compound (8A) (or, as an example, reaction of compound (7) with compound (8)) may be conducted in the presence of an activating agent. Non-limiting examples of activating agents are chloroformic acid esters (e.g., preferably methyl, ethyl or benzyl chloroformate); phosgenes such as diphosgene and triphosgene; and an acyl chloride, such as pivaloyl chloride. Step (a) may optionally further be conducted in the presence of a base.

The compound of formula (8A) which contains an activated acyl group, may be prepared in a separate step prior to step (a) and added to the reaction with compound (7A) or, alternatively, compound (8A) may be formed in-situ and reacted with compound (7A) in one step.

The step of converting compound (9A) to compound (I) may be conducted in the presence of a base, preferably an alkali metal alkoxide. In the case that compound (9A) is first converted to an acylated derivative (11A), the step of converting compound (11A) to compound (I) may be conducted in the presence of a base, and optionally further in the presence of a Lewis acid.

In some embodiments, the step of converting compound (9A) to compound (I) directly produces the salt of formula (I). In other embodiments, the salt can be converted back to the acidic (i.e., enol) form and, if desired, a base may be added to reform the salt. Thus, in one embodiment, the process of the invention further comprises the step of converting a compound of formula (I) to a salt thereof. For example, when the compound of formula (I) is Laquinimod of formula (1), the process further comprises converting Laquinimod into a salt thereof, preferably the sodium salt. In accordance with this embodiment, the process comprises the step of reacting Laquinimod (1) with a sodium containing base so as to obtain its sodium salt. The sodium containing base can be a sodium alkoxide such as sodium methoxide, sodium ethoxide, sodium tert-butoxide and the like. In one embodiment, the process for converting Laquinimod to its sodium salt comprises the following steps:

(i) suspending Laquinimod in an alcohol;

(ii) adding sodium alcoholate to form a clear solution;

(iii) concentrating the solution by partial removal of the solvent;

(iv) cooling the concentrated solution to form crystals; and (v) isolating the Laquinimod sodium crystals.

In other embodiments, the present invention provides a method of treating multiple sclerosis or an autoimmune disease selected from Crohn's disease, rheumatoid arthritis, insulin-dependent diabetes mellitus, Guillain Bane Syndrome, and Lupus, comprising the step of administering to a subject in need thereof a therapeutically effective amount of Laquinimod of formula (1), or pharmaceutically acceptable salts thereof, as prepared in accordance with the process described herein.

In yet other embodiments, the present invention relates to Laquinimod of formula (1), or pharmaceutically acceptable salts thereof, as prepared in accordance with the processes described herein, for use in treating multiple sclerosis or an autoimmune disease selected from Crohn's disease, rheumatoid arthritis, insulin-dependent diabetes mellitus, Guillain Barré Syndrome, and Lupus.

Certain intermediates produced by the process described herein are novel and represent further embodiments of the present invention. For example, in one embodiment, the present invention provides an intermediate compound represented by the structure of formula (7):

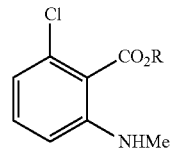

(7)

wherein R is an alkyl, aryl or alkylaryl, preferably wherein R is methyl, ethyl or benzyl.

In another embodiment, the present invention provides an intermediate compound represented by the structure of formula (8):

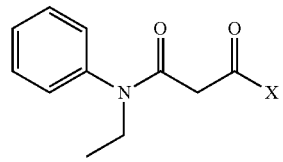

(8)

wherein X is a leaving group.

In another embodiment, the present invention provides an intermediate compound represented by the structure of formula (9):

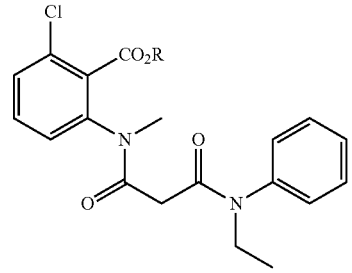

(9)

wherein R is an alkyl, aryl or alkylaryl, preferably wherein R is methyl, ethyl or benzyl.

In another embodiment, the present invention provides an intermediate compound represented by the structure of formula (10):

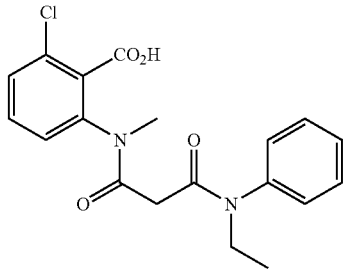

(10)

In another embodiment, the present invention provides an intermediate compound represented by the structure of formula (11):

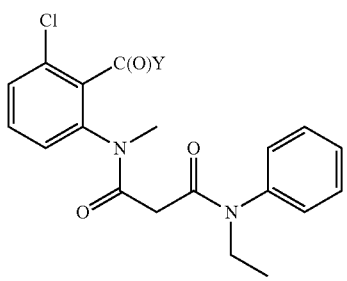
(11)

wherein Y is a leaving group.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to processes for the synthesis of quinoline-3-carboxamide derivatives of general formula (I), or salts thereof. A non-limiting example of such a process relates to the preparation of Laquinimod of structural formula (1), or its salts such Laquinimod sodium. The present invention further relates to certain intermediates formed in such processes.

Chemical Definitions:

An "alkyl" group refers to any saturated aliphatic hydrocarbon, including straight-chain, and branched-chain. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention.

An "aryl" group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. Each possibility represents a separate embodiment of the present invention.

An "alkylaryl" group is an alkyl group as defined herein bonded to an aryl group as defined herein. The aryl group can be unsubstituted or substituted through available carbon atoms with one or more groups defined hereinabove for alkyl.

The process of the invention for preparing quinoline-3-carboxamide derivatives of general formula (I) is illustrated in Scheme 2:

Scheme 2

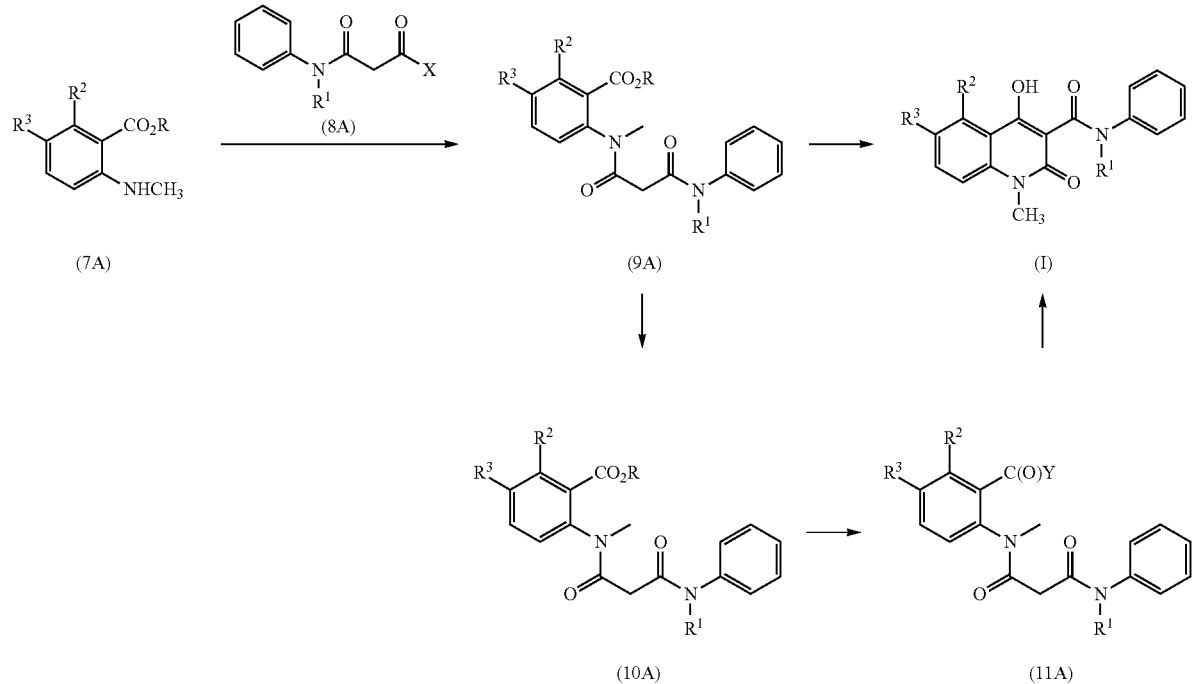

This process may be used to prepare Laquinimod of formula (1), as illustrated in Scheme 3:

Scheme 3

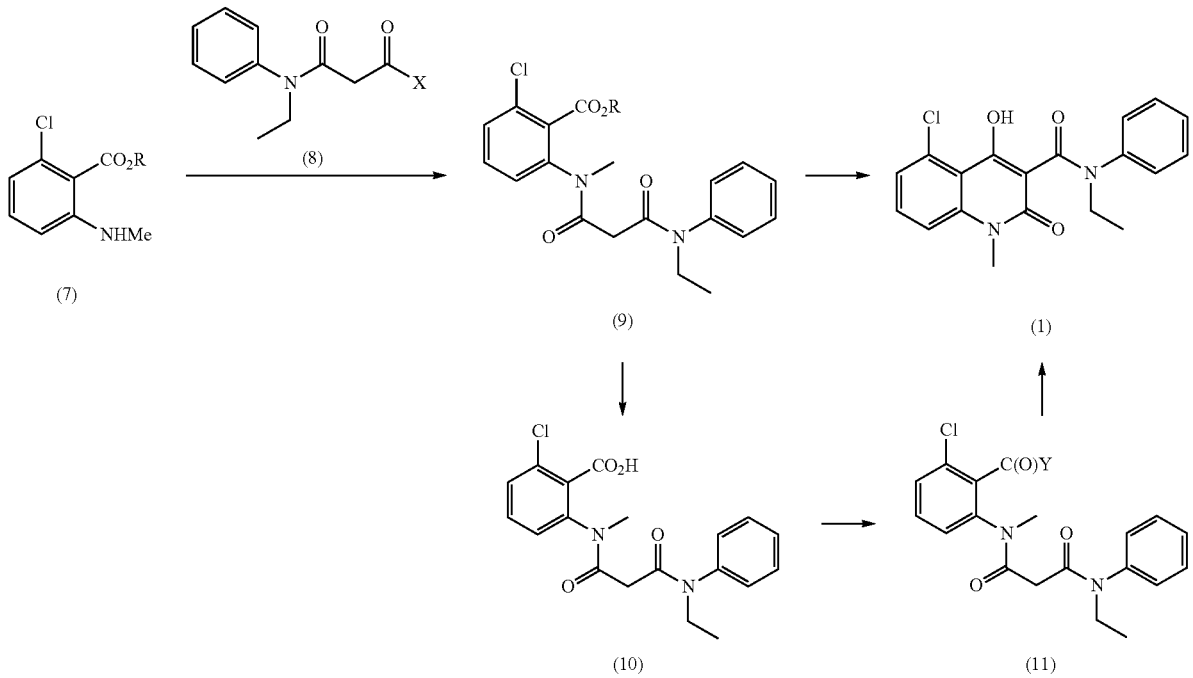

Further reference to each of the alternative embodiments will now be made. It is apparent to a person of skill in the art, however, that any description provided herein is representative in nature and should not be construed as limiting the broad scope of the present invention.

Step (a) of the process comprises reacting an anthranilate derivative of formula (7A) with a 3-oxopropanoic acid derivative of formula (8A), so as to obtain a compound of formula (9A). For example, when applied to prepare Laquinimod, this step comprises reacting N-methyl 6-chloroanthranilate (7) with 3-(ethyl(phenyl)amino)-3-oxopropanoic acid derivative (8), so as to obtain a compound of formula (9). R in compounds (7A), (9A), (7) or (9) is an alkyl, aryl or alkylaryl, preferably methyl, ethyl or benzyl. The substituent X in compounds (8A) or (8) is OH or a leaving group, such as halogen, O-sulfonyl (i.e., sulfonyloxy), OBt (O-benzotriazole), ONSu (Succinimido-oxy), or OC(O)$R^b$ (wherein $R^b$ is alkyl, aryl or alkylaryl, preferably, methyl, ethyl, isopropyl, t-butyl or phenyl and the like). A currently preferred leaving group is a halogen, e.g., Cl. Other examples of appropriate leaving groups are described hereinbelow.

N-methyl 6-chloroanthranilate (7) which is used here as a raw material (or other similar derivatives of formula (7A), can be produced from commercially available 6-chloroanthranilic acid as exemplified herein, and/or by well-known methods described in WO 2006/072370, WO 2002/028818, DE 3936229, U.S. Pat. No. 4,633,009, or Org. Lett, 2009, v. 11, No. 8, p. 1677-1680, the contents of each of which are incorporated by reference herein.

3-(Ethyl(phenyl)amino)-3-oxopropanoic acid (8, X=OH) (or other similar derivatives of formula 8A) can be produced from commercially available N-ethylaniline (or other N-alkylated anilines) and a malonic acid derivative (e.g., Meldrum's acid or monoalkyl malonate, such as monoethylmalonate or its corresponding acyl derivative) by procedures exemplified herein, and/or as described in, e.g., Tetrahedron Lett., 1989, v. 30, No. 23, p. 3073-3076; Chem. Pharm. Bull., 1985, v.33, p. 4878-4888; and Org. Lett., 2002, v. 4, No. 9, p. 1415-1418, the contents of each of which are incorporated by reference herein.

Step (a), when applied to the preparation of Laquinimod of formula (1), comprises converting N-methyl 6-chloroanthranilate (7) into a Laquinimod intermediate (9), by reacting N-methyl 6-chloroanthranilate (7) with a 3-(ethyl(phenyl)amino)-3-oxopropanoic acid derivative (8). More generally, step (a) comprises preparing a compound of formula (9A) by reacting an amine (7A) with a carboxylic acid (8A). For X=OH the process represents a reaction of an amine (7) or (7A) and carboxylic acid (8) or (8A) in which an amide bond is being formed. Amide bonds are typically synthesized from the condensation of carboxylic acids and ammonia or amines; however, the fusion of these two functional groups generally does not occur spontaneously at ambient temperature, as the elimination of water occurs only at high temperatures (e.g. >200° C.). Thus, although the process of the invention may be performed with compounds (8) or (8A) in which X=OH, it is usually preferred to first activate the carboxylic acid, a process that usually takes place by converting the —OH of the acid into a better leaving group prior to the treatment with the amine. In order to activate carboxylic acids, one can use so-called coupling reagents, which act as stand-alone reagents to generate compounds such as acid chlorides, (mixed) anhydrides, carbonic anhydrides or active esters, and the like. Hence, X can be any leaving group, such as, but not limited to:

(a) halogen, e.g., F, Cl, Br or I, more preferably, Cl.
(b) $OR^a$, wherein $R^a$ is an alkyl, such as a $C_1$ to $C_6$ straight or branched alkyl, an aryl, such as $C_6$ to $C_{10}$ aryl, or an alkylaryl, such as a $C_7$ to $C_{12}$ arylalkyl. Preferably, $R^a$ is a $C_1$ to $C_4$ straight or branched alkyl, phenyl or benzyl. More preferably, $R^a$ is methyl or ethyl.

(c) $OC(O)R^b$, wherein $R^b$ is alkyl, aryl or alkylaryl, preferably, methyl, ethyl, isopropyl, t-butyl or phenyl.

(d) azide ($N_3$).

(e) imidazolyl.

(f) $OR^c$, wherein $R^c$ is derived from 1-hydroxy-7-azabenzotriazole, 1-hydroxybenzotriazole, N-hydroxymaleimide, N-hydroxy-5-norbornene-2,3-dicarboxylic acid imide, N-hydroxyphthalimide, N-hydroxysuccinimide, N-hydroxysulfosuccinimide sodium salt, 2-, 3-, or 4-nitrophenol, pentafluorophenol, 2,4,5-trichlorophenol, ethoxyacetylene, and the like.

(g) $OR^d$ wherein $R^d$ is acyl, dialkyl- or diarylphosphate or other derivatives of phosphorus containing acid, boron containing derivatives and like.

(h) $OR^e$, wherein $R^e$ is isourea, derived from carbodiimides, such as dicyclohexyl carbodiimide (DCC), diisopropyl carbodiimide (DIC) 1-ethyl-3-(3'-dimethylamino) carbodiimide HCl salt (EDC or WSC) and like.

(i) $SR^f$, wherein $R^f$ is derived from 2-mercaptopyridine, 2-thiazoline-2-thiol and like.

(j) a derivative of cyanuric chloride or fluoride, such as 4-(4,6-dimethoxy-(1,3,5)-triazin-2-yl)-4-methyl-morpholinium chloride (DMTMM); isoxazolium salts such as N-ethyl-5-phenylisoxazolium-3'-sulfonate, N-ethylbenzisoxazolium tetrafluoroborate; Mukaiyama's reagent-2-chloro-1-methylpyridinium iodide and like, such as 2-bromo-3-ethyl-4-methylthiazolium tetrafluoro-borate (BEMT).

Each possibility for the substituent X as recited above represents a separate embodiment of the present invention.

In one embodiment, the activated acid derivative may be an acid chloride or other acid halide. Acid chloride formation can be performed by using reagents such as thionyl chloride, oxalyl chloride, phosgene, triphosgene, $POCl_3$, $PCl_3$, $PCl_5$, and the like, preferably thionyl chloride. The acid chloride is treated with N-methyl 6-chloroanthranilate (7) or more generally a compound of formula (7A) to produce the compound of formula (9) or more generally a compound of formula (9A). This reaction is typically performed in the presence of an organic solvent. Suitable organic solvents include, but are not limited to, halogenated hydrocarbons, aromatic hydrocarbons, esters, ethers, nitriles, ketones, amides and mixtures thereof; preferably dichloromethane, toluene, or diisopropyl ether. Each possibility represents a separate embodiment of the present invention.

Alternatively, an activated acid derivative may be a mixed anhydride of compound (8) or more generally a compound of formula (8A), which may be prepared by any of the methods known in the art, for example by treatment with methyl, ethyl or isopropyl chloroformate, pivaloyl chloride, or Boc anhydride and the like. Each possibility represents a separate embodiment of the present invention.

Preparation of amide (9) or (9A) may also be carried out by introducing an activation agent, for example, pivaloyl chloride into solution of a compound (8) or (8A) in an organic solvent in the presence of a base, so as to obtain a mixed anhydride, followed by reacting the mixed anhydride with amine (7) or (7A). The reaction is preferably carried out without separation and purification of the mixed anhydride. i.e. by "one-pot" synthesis. This reaction is typically performed in the presence of an organic solvent. Suitable organic solvents include, but are not limited to, halogenated hydrocarbons, aromatic hydrocarbons, esters, ethers, cyclic ethers, DMF, NMP and mixtures thereof; preferably methylene chloride. Each possibility represents a separate embodiment of the present invention. The organic base used in this step may be selected from the group consisting of triethylamine, diisopropylethylamine, N-methylmorpholine, pyridine, lutidine, and picoline, preferably pyridine. Each possibility represents a separate embodiment of the present invention.

Compound (9) or more generally compound (9A) is typically pure enough for use in the next step, but if necessary, it can be further purified by any suitable technique, for example, by crystallization (e.g., from an alcohol such as methanol, ethanol, propanol or isopropanol), or by column chromatography.

In the next step of the process, a compound of formula (I) is prepared by Dieckmann cyclization of compound (9A) in the presence of a base. For example, in one embodiment, Laquinimod (1) is prepared by cyclization of compound (9) in the presence of a base. Examples of suitable bases for this step include, but are not limited to, metal hydrides (e.g., alkali metal hydrides such as sodium hydride, potassium hydride, etc.), metal hydrocarbons (e.g., compounds having direct chemical bond between alkali metal and $C_{1-4}$ alkyl group such as n-butyllithium, etc.), alcoholates (e.g., compounds in which a hydroxy hydrogen of $C_{1-4}$ alcohols is replaced by a alkali metal such as sodium methoxide, sodium ethoxide, sodium t-butoxide, potassium methoxide, potassium ethoxide, potassium t-butoxide, lithium methoxide, lithium ethoxide, lithium t-butoxide, etc.), alkali metal hydroxides (e.g., NaOH, KOH, etc.), basic carbonates (e.g., alkali metal salts of carbonate such as sodium salt, potassium salt, etc., or alkali-earth metal salts of carbonate such as calcium salt, magnesium salt, etc.), basic bicarbonates (e.g., alkali metal salts of bicarbonate such as sodium salt, potassium salt, etc.), organic bases (e.g., trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene, etc.), basic resin and polymers such as Amberlyst A-26 resin (OH⁻ form) and preferably metal hydride compounds (e.g., sodium hydride, potassium hydride, etc.), alcoholates (e.g., NaOMe, NaOEt, t-BuONa, t-BuOK, etc.), basic resins. Currently preferred embodiments include alcoholates (e.g., NaOMe, NaOEt, t-BuONa, t-BuOK, etc.) and basic resins (e.g., Amberlyst A-26). Each possibility represents a separate embodiment of the present invention. The amount of base used for the above-mentioned reaction is about 0.1 to 100 equivalents, preferably about 1 to 5 equivalents based on the compound of formula (9).

Any solvent provided that it does not interfere with the reaction, may be used and includes, for example, halogenated solvents (e.g., methylene chloride, dichloroethane, chloroform, etc.), aliphatic hydrocarbons (e.g., n-hexane, etc.), aromatic hydrocarbons (e.g., benzene, toluene, etc.), ethers (e.g., tetrahydrofuran (THF), diethylether, etc.), polar solvents (e.g., dimethylformamide (DMF), dimethylsulfoxide (DMSO), etc.), alcohols (e.g., methanol, ethanol, propanol, isopropanol, n-butanol, 2-methoxyethanol, etc.) and like, preferably alcohols (e.g., methanol, ethanol, etc.). Each possibility represents a separate embodiment of the present invention.

In an alternative embodiment of the present invention, the intermediate of formula (9A) is not converted directly to a compound of formula (I) but, rather, compound (9A) is first saponified to convert the ester moiety $CO_2R$ to the corresponding carboxylic acid $CO_2H$ (compound 10A), followed by converting compound (10A) to its activated derivative compound (11A), in which the substituent Y can be any of the groups defined above for the substituent X, with each possibility defining a separate embodiment of the present invention. Compound (11A) is then cyclized to generate a compound of formula (I).

Saponification is the hydrolysis of an ester under basic conditions to form an alcohol and the salt of a carboxylic acid (carboxylates). The saponification step can be divided into two sub-steps:
i) the formation of the salt of compound (10A) by adding a base; and
ii) acidification of the reaction mixture by adding an acid, following by separation of compound of formula (10A).

Suitable bases for use in this reaction include, but are not limited to, alkali metal and alkaline earth carbonates and hydroxides, for example potassium bicarbonate, sodium bicarbonate, potassium carbonate, sodium carbonate, sodium hydroxide, potassium hydroxide, calcium hydroxide, and the like; primary, secondary, and tertiary amines such as piperidine, triethylamine, diisopropylethylamine, N-methylmorpholine, pyridine, lutidine and the like; ammonia and basic resins and, and the like. Bases to which current preference is given are hydroxides, such as NaOH or KOH. Each possibility represents a separate embodiment of the present invention. A suitable amount of base for saponification is, for example, at least one equivalent relative to corresponding ester, preferably from about 1 to about 5 equivalents; more preferably from about 1 to about 3 equivalents based on the amount of the ester. The base can be used as a solution in a suitable solvent, a preferred basic solution is a solution of inorganic hydroxide in alcohol, such as, but not limited to, a solution of sodium hydroxide in methanol.

The saponification is preferably carried out at a temperature range of about 20° C. to about 100° C., preferably from about 40° C. to about 70° C., more preferably from about 50 to about 55° C. The reaction time for the saponification is generally from about 15 minutes to about 48 hours, preferably from about 30 minutes to about 18 hours, and more preferably from about 1 to about 5 hours. The saponification can be carried out at normal, elevated or reduced pressure, preferably at normal pressure.

Suitable solvents for the saponification reaction include, but are not limited to alcohols, ethers, DMF, NMP, DMSO, water or suitable mixtures of these solvents. Some non-limiting examples of solvents are alcohols, such as methanol, ethanol, isopropanol or their mixtures with water. Each possibility represents a separate embodiment of the present invention.

After the formation of the salt of compound (10A), an acid is added so as to form the carboxylic acid moiety. The acid is added leading to an adjustment of the pH of the reaction mixture to a value of about 5-7.5, preferably to a value of about 6.5-7. Suitable acids are inorganic acids, such as hydrochloric acid, hydrobromic, phosphoric or sulfuric acid; or organic acids, such as formic acid, acetic acid, trifluoroacetic, methanesulfonic or propionic acid. Preference is currently given to inorganic acids such as hydrochloric acid. The acid is added typically at a temperature range of about −10° C. to about 75° C., especially of about 10° C. to about 25° C.

Compound (10A) can be then isolated from the reaction mixture by adding water to the reaction mixture to obtain two phases, separating the organic layer, and evaporating the organic layer to obtain a residue. Evaporation can be carried out at an elevated temperature of about 45° C. to about 60° C. and/or at a pressure of less than about one atmosphere.

Converting the —COOH group of compound (10A) to form an activated acid derivative (11A), preferably an acyl chloride (Y═Cl), can be performed by using the methods described above for the transformation of acid (8A; X═OH) to its activated acid derivative.

Finally, the cyclization of activated compound (11A) into a compound of formula (I) can be carried out in the presence of a base in an organic solvent. Any base and solvent used above for the Dieckmann cyclization described above can serve as a base and a solvent for the cyclization of compound (11A) to compound (I). Non-limiting examples of suitable bases are potassium carbonate in a polar solvent such as NMP, triethylamine or pyridine in chlorinated solvents such as dichloromethane, dichloroethane or in toluene.

The reaction can also be promoted by the addition of a Lewis acid, which includes, but not limited to $MgCl_2$, $ZnCl_2$, $AlCl_3$, $FeCl_3$, $BiCl_3$, $InCl_3$, $H_3BO_3$, $LaCl_3$, $NdCl_3$, $SmCl_3$, $DyCl_3$, $ErCl_3$, $YbCl_3$ and $Yb(OTf)_3$.

In one embodiment, this process is applied for the preparation of Laquinimod of formula (1). The process comprises the following steps:
a) saponification of ester (9) to acid (10);
b) converting acid (10) to an activated derivative (11) such as an acyl halogenide or any other suitable active ester; and
c) cyclization of thus obtained compound (11) to Laquinimod (1).

Any of the conditions described above for saponification of ester (9A) to carboxylic acid (10A), conversion of (10A) to an activated derivative (11A), and cyclization of (11A) to compound (I), are suitable for the process of converting ester (9) to Laquinimod (1).

The aforementioned process may directly yield the compound of formula (I) in its salt form. An acid can then optionally be added to convert the salt of compound (I) to the corresponding acidic form (i.e., enol) and, if desired, a base can be added to reform the salt form of compound (I). For example, when Laquinimod is prepared, the cycliczation step in the presence of a base may directly yield Laquinimod in its salt form. Optionally, an acid may be added to neutralize the salt and form Laquinimod in its enol form.

Next, if desired, Laquinimod can further be converted to its salt form, for example its sodium salt. Processes for the preparation of sodium salt of Laquinimod are disclosed in U.S. Pat. No. 6,077,851 and U.S. Pat. No. 6,875,869, the contents of each of which are incorporated by reference herein. According to the embodiments exemplified in U.S. Pat. No. 6,077,851, the sodium salt is obtained by suspending Laquinimod in ethanol, adding 5M sodium hydroxide solution to the suspension by adjusting the pH to 8-12, stirring the reaction mixture for 30 minutes at ambient temperature and recovering the precipitated Laquinimod sodium. In such a method the Laquinimod sodium is not dissolved in the solvent and any solid impurities, if present in the Laquinimod sodium suspension, are therefore not removed by filtration.

PCT Publication No. WO 2007/047863 discloses a process for the recrystallization of Laquinimod sodium comprising dissolving Laquinimod sodium in water to form an aqueous solution, concentrating the solution to form a concentrated solution, adding a water-miscible anti-solvent to the concentrated solution to form Laquinimod sodium crystals, and isolating the Laquinimod sodium crystals. The applicants state that Laquinimod sodium is slightly soluble in alcohols, but small amount of water in the alcohol significantly increases the solubility of Laquinimod sodium and can completely prevent crystallization. Therefore the addition of an anti-solvent is apparently essential for the sedimentation of Laquinimod sodium. Even in this improved process the yield of salt formation is varied from 70 to 90%.

PCT Publication No. WO 2010/001257 discloses a process for preparing Laquinimod sodium in polymorphic forms comprising suspending Laquinimod in a solvent (alcohol or ketone) followed by adding the suspension with an aqueous sodium hydroxide solution and then heating the resulting mass to form a clear solution. The obtained solution is optionally subjected to filtering to remove any extraneous matter or to carbon treatment or silica get treatment. The isolation of Laquinimod sodium in crystalline form is carried out by cooling, seeding, partial removal of the solvent from the solution, by adding an anti-solvent to the solution, or a combination thereof. The yield of the desired compound is ~70-80%.

Although any of the above methods can be used in the context of the present invention to convert Laquinimod to Laquinimod sodium, the present invention further provides an improved process for preparation of Laquinimod sodium comprising:

(i) suspending Laquinimod in an alcohol;
(ii) adding sodium alcoholate to form a clear solution;
(iii) concentrating the solution by partial removal of the solvent;
(iv) cooling the concentrated solution to form crystals; and
(v) isolating the Laquinimod sodium crystals.

Suitable alcohols to be used in a step (a) include, but not limited to, methanol, ethanol, propanol, isopropanol, n-butanol, 2-methoxyethanol, and the like, preferably, methanol and ethanol. Each possibility represents a separate embodiment of the present invention. A preferred sodium alcoholate to be used in step (b) is an alcoholate formed from sodium and the alcohol used at step (a). Formation of clear solution can be achieved by stirring Laquinimod with the sodium alcoholate in alcohol until full dissolution of Laquinimod at room temperature or, optionally, at reflux temperature followed by filtering the solution from any extraneous matter.

Step (c) comprises partial removal of the solvent by means known to a person of skill in the art, for example removal by evaporation at room temperature or under heating, at atmospheric pressure or under reduced pressure. The solution can be condensed to about 10-90% of its original volume, for example to about 10%, 15%, 20%, 25%, 30%, 35%, 40%, 45%, 50%, 55%, 60%, 65%, 70%, 75%, 80%, 85% or 90% of its original volume. Each possibility represents a separate embodiment of the present invention.

Step (d) is then executed by cooling the concentrated solution to a temperature of about 10° C. or below, for example to a temperature of 5° C., 0° C. or even lower.

The isolating step (e) may be carried out by methods such as filtration, filtration under vacuum, decantation, centrifugation, or a combination thereof. The substantially pure Laquinimod sodium crystals obtained by the above process are further dried to eliminate residual solvents. The selection of the drying equipment is well within the capabilities of a person of ordinary skill in the art. Drying can be carried out under reduced pressure such as 50-200 mm Hg, at temperatures such as about 35° C. to about 75° C. until the residual solvent content reduces to the desired level. The drying can be carried out for any desired time period that achieves the desired result, such as about 1 to 20 hours. Drying may also be carried out for shorter or longer periods of time depending on the product specifications. Temperatures and pressures will be chosen based on the volatility of the solvent being used and the foregoing should be considered as only a general guidance.

The process of preparing Laquinimod sodium is simple and uses only a single solvent, which can be easily recycled. Anhydrous process conditions facilitate the crystallization and the drying of the compound. The process provides Laquinimod sodium with desirable purity (>98.5%) and yield (>90%).

Other suitable salts of Laquinimod which can be prepared by the process described by the present application include but are not limited to lithium, potassium, magnesium, calcium, manganese, copper, zinc, aluminum and iron. Each possibility represents a separate embodiment of the present invention. Preferably the salt is a pharmaceutically acceptable salt. To generate these salts, Laquinimod is reacted with a suitable reagent so as to introduce the relevant cation, using methods known to a person of skill in the art.

Intermediates and Process for Preparation Thereof

Certain intermediates produced by the process described herein are novel and represent further embodiments of the present invention. For example, in one embodiment, the present invention provides an intermediate compound represented by the structure of formula (7) wherein R is an alkyl, aryl or alkylaryl, preferably wherein R is methyl, ethyl or benzyl.

In another embodiment, the present invention provides an intermediate compound represented by the structure of formula (8) wherein X is a leaving group.

In another embodiment, the present invention provides an intermediate compound represented by the structure of formula (9) wherein R is an alkyl, aryl or alkylaryl, preferably wherein R is methyl, ethyl or benzyl.

In another embodiment, the present invention provides an intermediate compound represented by the structure of formula (10).

In another embodiment, the present invention provides an intermediate compound represented by the structure of formula (11) wherein Y is a leaving group.

The following examples are given for the purpose of illustrating the present disclosure and should not be considered as limitation on the scope or spirit of the invention.

EXPERIMENTAL SECTION

Certain compounds which are representative of this invention were prepared as per the following examples and reaction sequences. No attempt has been made to optimize the yields obtained in any of the reactions. Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, column chromatography, preparative HPLC and the like.

Example 1

Preparation of Laquinimod Sodium

A. Preparation of methyl 2-chloro-6-methylamino-benzoate (II) by monomethylation of the amino group of 2-amino-6-chloro-benzoic acid and its subsequent esterification (Scheme 4)

Scheme 4

STEP 1:

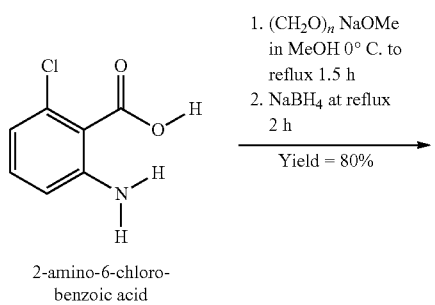

STEP 2

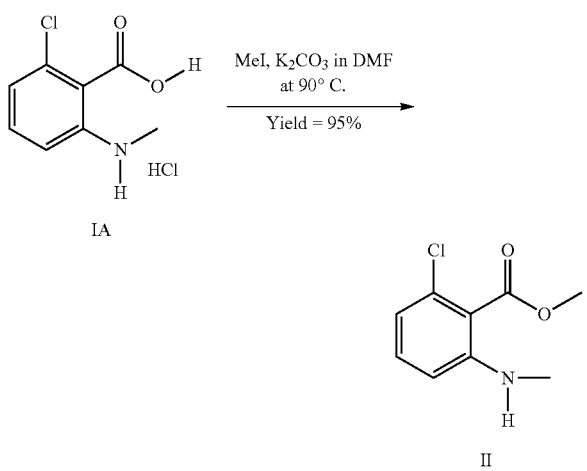

Step 1: Preparation of 2-chloro-6-methylamino-benzoic acid hydrochloride salt (I)

Anhydrous methanol (10 ml) was charged in a dry round bottom flask at 20-25° C. under nitrogen atmosphere. 2-amino-6-chloro-benzoic acid (201 mg, 1.17 mmol) was added, followed by paraformaldehyde (351.1 mg, 1.17 mmol). The mixture was stirred and cooled to 0-5° C. A 30 wt % solution of sodium methoxide (0.975 ml, 5.26 mmol) was added dropwise, keeping the temperature at 0-5° C. while stirring. The mixture was allowed to warm to room temperate (r.t.). Then, the resulting solution was heated to reflux for 1.5 h, then cooled to r.t. Sodium borohydride (209.1 mg, 5.5 mmol) was added in one portion, and the resulting mixture was heated to reflux for 2 h, then cooled to r.t. The reaction was concentrated by removal of solvent under reduced pressure. Chloroform (30 ml) and DM water (20 ml) were added, the mixture was cooled to 0-5° C., and the pH was adjusted to pH=2-3 with 1N HCl while stirring. The organic phase was separated and kept aside. The extraction step with chloroform (30 ml) was repeated twice more, the organic phases were combined and dried over sodium sulfate. The solvent was removed under reduced pressure resulting in a yellowish solid. Yield: 80%. The purity of the isolated product (Intermediate I-A) was 97% (HPLC, area %).

Analytical Characterization:

$^1$H-NMR (300 MHz, CDCl$_3$) 7.24 (m, 1H), 6.72 (d, J=7.5 Hz, 1H), 6.59 (d, J=8.4 Hz, 1H), 2.88 (s, 3H).

MS: MH+: 186

Step 2: Preparation of methyl 2-chloro-6-methylamino-benzoate (II)

Anhydrous dimethylformamide (29 ml, 5.5 mmol) was added to a dry round bottom flask, at 20-25° C. under nitrogen atmosphere. 2-chloro-6-methylamino-benzoic acid (2.7 g, 12.15 mmol) (Intermediate-IA from Step 1) was added at 20-25° C., followed by anhydrous potassium carbonate (2.517 g, 18.24 mmol), and the resulting suspension was stirred. The mixture was heated to 90-95° C. and stirred for 30 min. A solution of methyl iodide (1.136 ml, 18.24 mmol) in anhydrous dimethylformamide (10 ml) was prepared and added to the mixture over a period of about 1 hour, keeping the temperature at 90-95° C. and stirring. The mixture was stirred at 90-95° C. for 30 minutes, then cooled to r.t. DM water (300 ml), hexane (56 ml) and ethyl acetate (24 ml) were added, the reaction was mixed and the phases separated. The organic phase was separated and kept aside. The extraction step with hexane (56 ml) and ethyl acetate (24 ml) was repeated twice more, the organic phases were combined and washed 3 times with 100 ml brine, then dried over sodium sulfate and filtered. The solvent was removed under reduced pressure resulting in a yellowish oil. Yield: 95%. The purity of the isolated product was 93% (HPLC, area %).

Analytical Characterization:

$^1$H-NMR (300 MHz, CDCl$_3$) 7.18 (t, 1H), 6.69 (d, J=7.5 Hz, 1H), 6.55 (d, J=6.3 Hz, 1H), 3.92 (s, 3H), 2.84 (s, 3H).

MS: MH+: 200

B. Preparation of 3-(ethyl(phenyl)amino)-3-oxo-propanoic acid (IV) by condensation between methyl-3-chloro-3-oxo-propanoate and N-ethyl aniline, and subsequent hydrolysis (Scheme 5)

Scheme 5

STEP 3

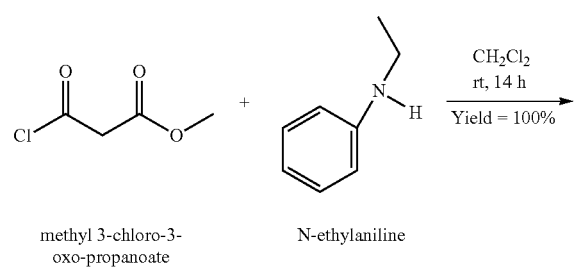

methyl 3-chloro-3-oxo-propanoate     N-ethylaniline

21

-continued

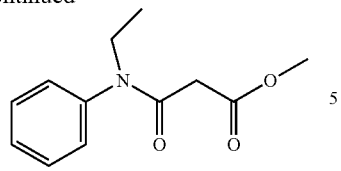

III

STEP 4

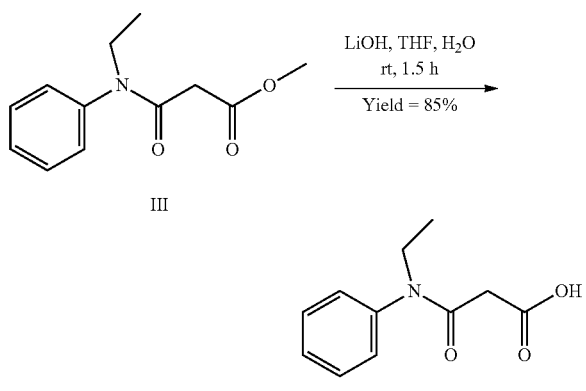

Step 3: Preparation of methyl
3-(ethyl(phenyl)amino)-3-oxo-propanoate (III)

Dichloromethane was added to a dry round bottom flask at 20-25° C. under nitrogen atmosphere. Methyl 3-chloro-3-oxo-propanoate (2.59 ml, 24.15 mmol) was added, followed by N-ethylaniline (2.97 ml 24.13 mmol), and the solution was stirred at r.t. for 14 h, then the solvent was removed under reduced pressure to obtain a yellowish oil. Yield: 100%. The purity of the isolated product: 98% (HPLC, area %).
Analytical Characterization:
$^1$H-NMR (300 MHz, CDCl$_3$) 7.40 (m, 3H), 7.19 (m 2H), 3.79 (m, 2H), 3.66 (s, 3H), 3.16 (s, 2H), 1.13 (t, J=7.2 Hz, 3H).
MS: MH+: 222; MNa+: 244

Step 4: Preparation of
3-(ethyl(phenyl)amino)-3-oxo-propanoic acid (IV)

Tetrahydrofuran (24 ml) and methyl-3-(ethyl(phenyl)amino)-3-oxo-propanoate (III) (5.338 g, 24.13 mmol) were added to a round bottom flask. A solution of lithium hydroxide (1.16 g, 48.26 mmol) DM water (23.2 ml) was prepared and added to the reaction in one portion. The reaction was stirred at r.t. for 1.5 h, then the solvent was removed under reduced pressure. Ethyl acetate (40 ml) and water (20 ml) were added, the mixture was cooled to 0-5° C., and the pH was adjusted to pH=2-3 with 1N HCl while stirring. The organic phase was separated and kept aside. The extraction with ethyl acetate (40 ml) and DM water (20 ml) was repeated twice more, and the organic phases were combined and dried over sodium sulfate and filtered. The solvent was removed under reduced pressure to obtain a yellowish solid. Yield: 85%. The purity of the isolated product: 95% (HPLC, area %).
Analytical Characterization:
$^1$H-NMR (300 MHz, CDCl$_3$) 7.44 (m, 3H), 7.16 (m 2H), 3.2 (q, J=7.2 Hz, 2H), 3.06 (s, 3H), 1.18 (t, J=7.2 Hz, 3H).
MS: MH+: 208; MNa+: 230

22

C. Condensation between Intermediates II and IV and Inter-IV to give methyl 2-chloro-6-[[3-(ethyl (phenyl)amino)-3-oxo-propanoyl]-methylamino] benzoate (V) (compound 9), Scheme 6

Scheme 6

STEP 5:

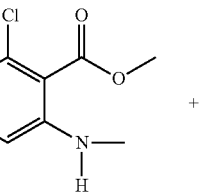

II

+

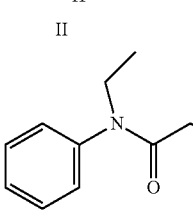

IV

1. Pivaloyl chorid, Py
0° C.
2. rt 14 h
Yield = 80%

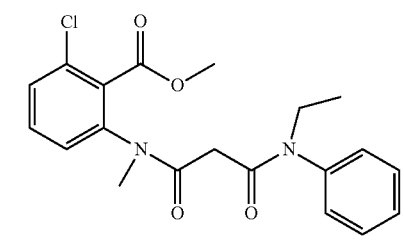

V

Step 5

Anhydrous dichloromethane (50 ml), 3-(ethyl(phenyl) amino)-3-oxo-propanoic acid (IV) (2.634 g, 12.71 mmol) and pyridine (2.8 ml, 34.66 mmol) were added to a round bottomed flask at 20-25° C. under nitrogen atmosphere, and the resulting mixture was stirred at r.t. for 0.5 h, then cooled to 0-5° C. while stirring. Pivaloyl chloride (2.1 ml, 17.32 mmol) was added dropwise while keeping the temperature below 5° C., and the mixture was further stirred for 1 h at 0-5° C. A solution of methyl 2-chloro-6-methylamino-benzoate (II) (2.3064 g, 11.55 mmol) in anhydrous dichloromethane (11 ml) was prepared and added to the reaction at 0° C. The reaction was allowed to warm up to r.t. and stirred at this temperature for 14 h, then concentrated under reduced pressure. Ethyl acetate (180 ml) and a solution of 0.1N HCl (80 ml) were added, the phases were mixed and the aqueous phase was discharged. The wash steps with 0.1N HCl (80 ml) was repeated twice more, then the reaction was washed twice with 80 ml brine and three times with 80 ml NaHCO$_3$. The organic phases were dried over sodium sulfate and filtered and the solvent was removed under reduced pressure to afford a residue, which was recrystallized from isopropanol to obtain an off-white solid. Yield: 80%. The purity of the isolated product was 100% (HPLC, area %).

Analytical Characterization:

$^1$H-NMR (300 MHz, CDCl$_3$) 7.37 (m, 5H), 7.24 (m, 1H), 6.94 (m, 2H), 3.74 (s, 3H), 3.2 (q, J=4.8 Hz, 2H), 3.13 (s, 3H), 2.94 (s, 2H), 1.18 (t, J=7.2 Hz, 3H).

MS: MH+: 389; MNa+: 411

D. Preparation of Laquinimod Sodium by Intramolecular Cyclization of Compound (V) (Scheme 7)

Scheme 7

STEP 6:

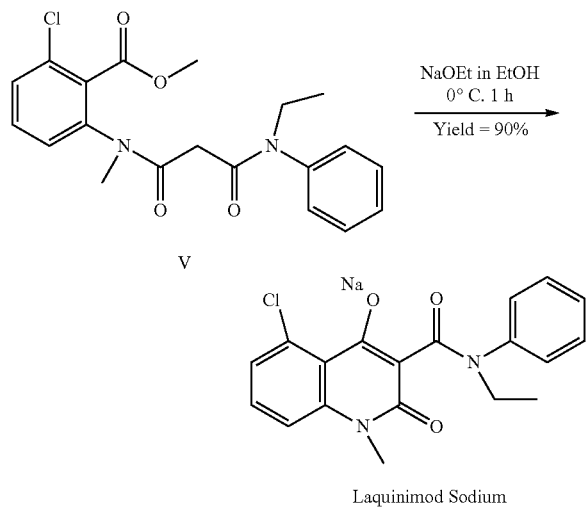

Step 6

Methyl 2-chloro-6-[[3-(ethyl(phenyl)amino)-3-oxo-propanoyl]-methyl-amino]benzoate (Inter-V) (1.5 g, 3.858 mmol) and anhydrous ethanol (40 ml) were added to a round bottom flask at 20-25° C. under nitrogen atmosphere, and the mixture was stirred under nitrogen till a clear solution was obtained. The solution was cooled to 0-5° C., and a 21 wt % solution of sodium ethoxide was added (1.51 ml, 4.051 mmol) keeping the temperature at 0-5° C. while stirring. The mixture was stirred for an additional 1 h at 0-5° C., and the flask was placed in the refrigerator for 12 hours. The precipitate was filtered to obtain a white powder which was dried at 25° C. under vacuum. Yield: 90%. The purity of the isolated product was 100% (HPLC, area %).

Analytical Characterization:

$^1$H-NMR (300 MHz, DMSO) 7.29 (m, 2H), 7.17-7.05 (m, 5H), 6.82 (m, 1H), 3.67 (m, 2H), 3.26 (s, 3H), 1.01 (t, J=7.2 Hz, 3H).

MS: MH+: 357; MNa+: 379

Example 2

Preparation of methyl 2-chloro-6-(3-(ethyl(phenyl) amino)-N-methyl-3-oxopropanamido)benzoate (9)

A suspension of 3-(ethyl(phenyl)amino)-3-oxopropanoic acid (8) (11 mmol), methylene chloride (50 ml) and pyridine (2.43 ml, 30 mmol) was stirred at room temperature for 30 minutes. Then the solution was chilled to 0° C. and pivaloyl chloride (1.84 ml, 15 mmol) was added drop-wise to keep the temperature below 5° C. After stirring for 10 minutes at 0° to 5° C., N-methyl 6-chloroanthranilate (7) (10 mmol) was added. After stirring at 0° C. for one hour the reaction was allowed to proceed overnight at room temperature (about 20 hours). The following day the reaction solution was diluted with ethyl acetate (100 ml), washed successively with 0.1 N hydrochloric acid (three times, 50 ml each time), brine (50 ml), saturated aqueous sodium bicarbonate (three times, 50 ml each time) and brine (50 ml), dried over magnesium sulfate, filtered and evaporated.

Compound (9) is pure enough for use on the next step, but if necessary, it can be further purified by any suitable technique, for example, by crystallization or by column chromatography.

Example 3

Preparation of Laquinimod (1)

a). To (9) (5 mmol) dissolved in dry ethanol (25 ml) at 5° C. was added sodium ethoxide (0.37 g, 5.2 mmol). The mixture was stirred at this temperature for 1 h, and then at room temperature under TLC control. After completion of the reaction (~2-3 h) [if the reaction was not completed by this time, the mixture was further refluxed for an additional 1-2 h], water (100 ml) was slowly added followed by a drop-wise addition of 1.0 N hydrochloric acid (6 ml) with stirring. After 30 minutes at 5° C., the crystals were collected by filtration, washed with water, and dried at 40° C. under vacuum to give (1) in 79% yield with an assay of 98.6%.

b). To a stirred solution of (9) (10 mmol) in anhydrous THF (50 ml) was added sodium methoxide (3.6 mmol as 0.5 M in MeOH) portion-wise under N$_2$ atmosphere, and the resulting mixture was refluxed for 2 h. The mixture was cooled and the solvent was evaporated partially to afford a concentrated solution, containing the insoluble salt. This was dissolved in a mixture of methanol (30 ml), 10M NaOH (1.07 mL, 10.7 mmol), and water (15.0 ml). Then, 5M HCl (aq) (2.4 ml, 12.0 mmol) was added. The crystalline precipitate was collected, washed with cold methanol and dried to afford the desirable compound in 87% yield with an assay of 98.9%.

c). Solution of (9) (10 mmol) in 50 ml of methanol was stirred in the presence of Amberlyst A-26 (OH$^-$ form) under TLC control. After completion of the reaction (~15-16 h), 1 M NaOH (50 ml) was added and the mixture was stirred for 30 min at room temperature, then filtered. The pH of filtrate was adjusted to 6.5 with 2 M HCl, and the solution was filtered through Celite followed by acidification to pH 1.5 and stirring for 1-2 h at room temperature, and for 2-3 h at 5° C. The precipitated product was filtered, washed with cold methanol and dried under reduced pressure. 71% yield of product was obtained with an assay of 97.6% d). Dry MgCl$_2$ (0.47 g, 5.0 mmol) was added to 5 mL of CH$_2$Cl$_2$, stirred and the mixture was cooled to 0-5° C. Pyridine (0.80 mL, 10.0 mmol) was added, and the cold mixture was stirred for 15 min Neat acid chloride (11) (5 mmol) was then slowly added. The cold reaction mixture was allowed to stir for 15 min. The reaction mixture was then warmed to room temperature and stirred under TLC control. After completion of the reaction (~1 h) the mixture was quenched with ice-water. The pH of the filtrate was adjusted to 6.5 with 2 M HCl, and the solution was filtered through Celite followed by acidification to pH 1.5 and stirring for 1-2 h at room temperature, and for 2-3 h at 5° C. The precipitated product was filtered, washed with cold methanol and dried at reduced pressure. 64% yield of product was obtained with an assay of 90.8%

Example 4

Preparation of Laquinimod (1) Sodium

N-Ethyl-N-phenyl-1,2-dihydro-4-hydroxy-5-chloro-1-methyl-2-oxoquinoline-3-carboxamide (15 g) was suspended in methanol (100 ml) at 20-25° C. under stirring followed by the addition of a methanolic solution of sodium methoxide (2.3 g of MeONa in 10 ml of MeOH) at 20-25° C. The reaction was then stirred for 15-30 minutes at 25-30° C. The resulting solution was filtered and the methanol was partially distilled off under vacuum using rotary evaporator at 50-55° C. to afford a concentrated Laquinimod (1) sodium solution. The resulting mass was cooled to 0-5° C. followed by stirring for 2 hours at the same temperature. The thus formed white colored solid was filtered, washed with chilled methanol (20 ml) and then dried under vacuum at 60-65° C. to yield 15 g (94%) of Laquinimod sodium, HPLC Purity: 99.6%.

In case after stirring for 1 h at 0-5° C. no crystals were formed, the resulting filtrate was warmed to 25-30° C. and seeded with pure Laquinimod sodium (0.175 gm), then stirred for 4 hours at 25-30° C. and 2-3 hours at 0-5° C.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

What is claimed is:

1. A compound represented by the structure of formula (9):

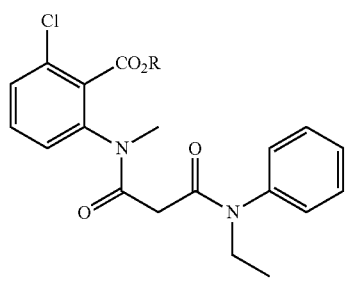

(9)

wherein R is an alkyl, aryl or alkylaryl.

2. The compound according to claim 1, wherein R is methyl, ethyl or benzyl.

3. A compound selected from the group consisting of:
a compound represented by the structure of formula (10):

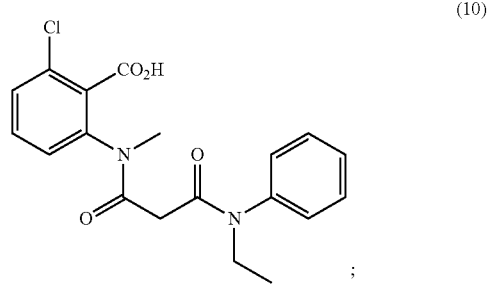

(10)

and a compound represented by the structure of formula (11):

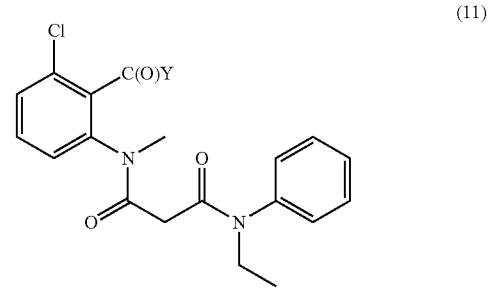

(11)

wherein Y is a leaving group.

4. The compound according to claim 3, wherein Y is selected from the group consisting of halogen, sulfonyloxy, O-benzotriazole (OBt), succinimido-oxy (ONSu), $OR^a$ wherein $R^a$ is an alkyl, aryl or alkylaryl, and $OC(O)R^b$ wherein $R^b$ is an alkyl, aryl or arylalkyl.

* * * * *